United States Patent [19]

Deller et al.

[11] Patent Number: 5,512,529
[45] Date of Patent: Apr. 30, 1996

[54] CATALYST FOR THE SELECTIVE HYDROGENATION OF AROMATIC HALONITRO COMPOUNDS TO AROMATIC HALOAMINES AND A PROCESS FOR ITS PRODUCTION

[75] Inventors: Klaus Deller, Hainburg; Bertrand Despeyroux, Hanau; Erik Peldszus, Hasselroth; Beate Kleinwaechter, Hanau, all of Germany

[73] Assignee: Degussa Aktiengesellschaft, Frankfurt, Germany

[21] Appl. No.: 71,250

[22] Filed: Jun. 4, 1993

[30] Foreign Application Priority Data

Jun. 9, 1992 [DE] Germany ............ 42 18 866.0

[51] Int. Cl.$^6$ .................... B01J 21/18; B01J 23/42; B01J 23/72
[52] U.S. Cl. ............... 502/184; 502/185; 502/331; 502/339; 502/345
[58] Field of Search .................. 502/184, 185, 502/339, 345, 331

[56] References Cited

U.S. PATENT DOCUMENTS

| | | | |
|---|---|---|---|
| 3,546,297 | 12/1970 | Kosak | 260/580 |
| 3,666,813 | 5/1972 | Hindin et al. | 502/325 |
| 3,726,915 | 4/1973 | Pohlmann et al. | 502/184 |
| 3,897,499 | 7/1975 | Vollheim et al. | 260/580 |
| 3,928,451 | 12/1975 | Krishnan | 260/580 |
| 4,111,842 | 9/1978 | van Montfoort et al. | 502/184 |
| 4,231,898 | 11/1980 | Mauldin et al. | 502/225 |
| 4,265,786 | 5/1981 | Eberly et al. | 502/215 |
| 4,507,494 | 3/1985 | Miyazaki et al. | 502/339 |
| 4,528,385 | 7/1985 | aus der Funten et al. | 549/307 |
| 4,716,087 | 12/1987 | Ito et al. | 502/331 |
| 4,780,300 | 10/1988 | Yokoyama et al. | 502/345 |
| 4,874,888 | 10/1989 | Shiomi et al. | 502/185 |
| 5,132,452 | 7/1992 | Deller et al. | 562/531 |
| 5,171,644 | 12/1992 | Tsou et al. | 502/155 |
| 5,258,340 | 11/1993 | Augustine et al. | 502/184 |
| 5,314,760 | 5/1994 | Tsou et al. | 502/101 |

FOREIGN PATENT DOCUMENTS

| | | |
|---|---|---|
| 0027979 | 5/1981 | European Pat. Off. . |
| 0496446 | 7/1992 | European Pat. Off. . |
| 2042368 | 4/1971 | Germany . |
| 2150220 | 4/1974 | Germany . |
| 3823301 | 11/1989 | Germany . |
| 2024643 | 1/1980 | United Kingdom . |
| 2052294 | 1/1981 | United Kingdom . |

OTHER PUBLICATIONS

Salek et al., Przemysl Chemiczny 58, (1979) 8.
Anderson et al., "Selektive Hydrierung mit neuen Platinkatalysatoren", Chemie–Technik, 18, 1989 pp. 40, 43, 44.

Primary Examiner—Anthony McFarlane
Attorney, Agent, or Firm—Beveridge, DeGrandi, Weilacher & Young

[57] ABSTRACT

A modified supported noble metal catalyst is disclosed for the selective hydrogenation of aromatic halonitro compounds to form aromatic haloamines. The support consists of active carbon. The active component is platinum modified with copper. The new catalyst is distinguished by good selectivity and a high yield.

20 Claims, 1 Drawing Sheet

Low Pressure hydrogenation of 3, 4 DCNB

CATALYST FOR THE SELECTIVE HYDROGENATION OF AROMATIC HALONITRO COMPOUNDS TO AROMATIC HALOAMINES AND A PROCESS FOR ITS PRODUCTION

INTRODUCTION AND BACKGROUND

This invention relates to a heavy-metal-modified noble metal catalyst on a fine-particle carbon support for the hydrogenation of aromatic halonitro compounds to aromatic haloamines characterized by good activity, selectivity and yields. In a further aspect, the present invention also relates to the process of producing said catalysts.

Aromatic haloamines are important starting materials for the production of pharmaceuticals, dyes, pesticides and herbicides. They are produced from the corresponding aromatic halonitro compounds, for example by catalytic hydrogenation. The hydrogenation is normally carried out using a solvent to convert the solid aromatic halonitro compounds into the liquid phase. Typical hydrogenation conditions are reaction temperatures of 25° to 250° C. and hydrogen pressures of 1 to 350 bar. Such hydrogenation reactions are well known in the art.

The catalytic hydrogenation is attended by the problem that not only is the nitro group reduced to the amino group, but the halogen atoms are also substituted by hydrogen atoms, thereby resulting in the formation of the corresponding hydrohalide acid. The acid formed, such as hydrochloric acid, causes corrosion in the reactor and, accordingly, has to be avoided by using a selective catalyst which hydrogenates only the nitro group.

Attempts have been made in the past to avoid the dehalogenation by using supported noble metal catalysts modified by suitable additives to improve their selectivity.

Suitable supports are carbon black, particularly acetylene black and active carbon. Platinum is mainly used as the noble metal component. Although palladium has better activity than platinum, it also has poorer selectivity. Selectivity can be improved by modification of the catalyst with sulfur or heavy metals.

Salek et al. (A. Salek, J.M. Berak, S. Tobola, W. Ormaniec, A. Teichert: Przemysl Chemiczny 58 (1979) 8; 425– 427) report on studies to improve the activity and selectivity of a Pt/acetylene black catalyst in the hydrogenation of 3,4-dichloronitrobenzene. They arrive at the conclusion that good activity and selectivity can be obtained if the platinum content of the catalyst, based on the weight of the support, is at least 5% by weight, 15% by weight aniline is added to the reaction mixture and the catalyst is modified by 0.25 to 1% copper (where platinum and copper are simultaneously precipitated). Modification of the catalyst with copper produces an initially rapid reduction in the chloride concentration in the aqueous phase with increasing copper content and a slow reduction in activity. With 0.25% by weight copper, the chloride content is still above 2% by weight and only falls below 0.5% by weight where more than 0.5% by weight copper is used for modification. Modification of the catalyst with iron adversely affects selectivity. Salek et al. do not discuss the production of their catalysts in detail. The metal components were deposited onto the carbon black support by precipitation of the metal hydroxides from a solution of the metal salts with an $NaHCO_3$ solution. The temperature prevailing during this process is not mentioned. The catalysts would appear to have been used for the hydrogenation without preliminary reduction.

Generally, the use of catalysts based on carbon black supports on an industrial scale is problematical on account of filtration problems during the wet chemical production of the catalysts and during their use in the process.

DE-OS 20 42 368 describes lead-, bismuth- or silver-modified Pt/C catalysts. The optimum platinum content of the catalyst is said to be 5% by weight. Unmodified catalysts lead to the complete elimination of chlorine in the hydrogenation of 2,5-dichloronitrobenzene. In contrast to the works of Salek et al., modification with 5% by weight copper still produced a chlorine elimination of 75% which is probably attributable to the fact that no aniline is used in DE-OS 20 42 368 to prevent the elimination of chlorine. Only the addition of 5% by weight lead, bismuth or silver reduced the elimination of chlorine to below 1%.

British patent application GB 2,024,643 describes a platinum catalyst on acetylene black which is modified with iron to improve its activity and to reduce dehalogenation and the formation of hydroxyl amine. The support material is optimally charged with 5% by weight platinum, a range of 2:1 to 16:1 being disclosed for the molar ratio of iron to platinum which corresponds to a ratio by weight of approximately 1:2 to 4:1. According to the British patent application, the carbon black supports are required to show minimal porosity and, accordingly, a relatively small specific surface of less than 300 $m^2/g$. A carbon black with a specific surface of only 35 $m^2/g$ is used in the Examples. 70% of the particles of this support are smaller than 1 μm in size. According to the application in question, a high activity of the catalyst is achieved by optimal deposition of the catalytically active components platinum and iron in fine-particle form on the fine-particle, non-porous carbon black particles. To this end, platinum and iron first have to be precipitated as oxides, hydroxides or carbonates from an aqueous solution of the salts of the metal components at a temperature of approximately 90° C. in a suspension of carbon black and subsequently reduced with formaldehyde at room temperature.

If the platinum and iron are to be optimally distributed over the carbon black particles, it is crucially important that reduction is carried out at room temperature. Reduction at 90° C. gives much poorer results.

The British patent application identified above also describes comparison tests with support materials having larger surfaces, namely an active carbon (support of control F) having a specific surface of 500 $m^2/g$ and a carbon black support (support of control G) having a specific surface of 1050 $m^2/g$. 70% of the particles of the active carbon had a particle size below 30 μm while 70% of the particles of the carbon black support were larger than 10 μm in size. The catalyst on active carbon showed poor activity and resulted in a hydrogenation time of 133 minutes as against 84 minutes where the small surface carbon black support was used. Hydrogenation with the large surface carbon black support actually had to be terminated after 130 minutes because of excessive acid formation.

The articles "Platinkatalysatoren für die Hydrierung von Nitrobenzolen (Platinum Catalysts for the Hydrogenation of Nitrobenzenes)" by J. Strutz and E. Hopf in Chem. Ing. Tech. 60 (1988) 4, 297–298 and "Selektive Hydrierung mit neuen Platinkatalysatoren (Selective Hydrogenation with New Platinum Catalysts)" by J.B.F. Anderson, K.G. Griffin and R.E. Richards in Chemie-Technik, 18 (1989), 5, 40–44 describe pure platinum hydrogenation catalysts on active carbon supports. Although J.B.F. Anderson et al. achieve good selectivities with their catalyst charged with 1% platinum, they do not mention the yields obtained. J. Strutz and E. Hopf also report on catalysts charged with 1% platinum. However, the yields they obtained are inadequate.

The known catalysts described above for the hydrogenation of aromatic halonitro compounds to aromatic haloamines are unsatisfactory. In some cases, they involve the use of very large quantities of noble metal, in addition to which their selectivity and yield are inadequate.

Accordingly, an object of the present invention was to provide a catalyst for the hydrogenation of aromatic halonitro compounds to form aromatic haloamines which would be distinguished from the known catalysts by a low noble metal demand and by improved activity and selectivity. Another object of the invention was to provide a process for the production of this catalyst.

SUMMARY OF THE INVENTION

In attaining the above and other objects, one feature of the invention has been provided by a modified noble metal supported catalyst for the selective hydrogenation of aromatic halonitro compounds to form aromatic haloamines containing a support of carbon, platinum metal as the catalytically active component and copper as the modifier. The catalyst is characterized in that the support consists of active carbon; the platinum is present in a quantity of 0.1 to 5.0% by weight and preferably in a quantity of 0.5 to 3.5% by weight, based on the active carbon support, and the ratio by weight between the platinum and the copper which is simultaneously present is 5:1 to 20:1, preferably 10:1. It is a further feature that platinum and copper are present in finely distributed form on the active carbon.

The catalyst of the invention has particularly favorable properties when the average particle diameter of the active carbon is 15 to 30 µm, its specific surface is larger than 500 $m^2/g$ and its total pore volume is greater than 0.5 ml/g.

Another feature of the present invention has been provided by a process for the production of a noble metal supported catalyst by impregnation of the support material suspended in water with compounds of a catalytically active noble metal component and a modifying metal by precipitation of these compounds from aqueous solutions of readily soluble compounds thereof, reduction, filtration and washing of the catalyst. The process of this invention is characterized in that the aqueous suspension contains 5 to 30% by weight active carbon as the catalyst support; the noble metal component is platinum and the modifying metal is copper. Both platinum and copper are added to the suspension in the form of a solution of water-soluble platinum compounds, preferably hexachloroplatinic acid, and a water-soluble copper salt, preferably copper acetate. The content of platinum metal and copper metal in the solution is gauged to correspond to the desired charge of the quantity of active carbon used. The suspension is heated with stirring to 70° to 100° C. together with the solution of the water-soluble platinum and copper compounds before platinum and copper are simultaneously deposited on the active carbon by addition of a base, such as for example sodium carbonate or sodium hydroxide in the form of their sparingly soluble compounds. Subsequently they are reduced at the same temperature by addition of a reducing agent, such as hydrazine, sodium formate, sodium boranate or formaldehyde, preferably formaldehyde.

BRIEF DESCRIPTION OF THE DRAWING

The present invention will be further understood with reference to the drawing which is a graphical representation of the low pressure hydrogenation process with respect to reaction time, dehalogenation rate versus the copper context.

DETAILED DESCRIPTION OF INVENTION

Figure 1:
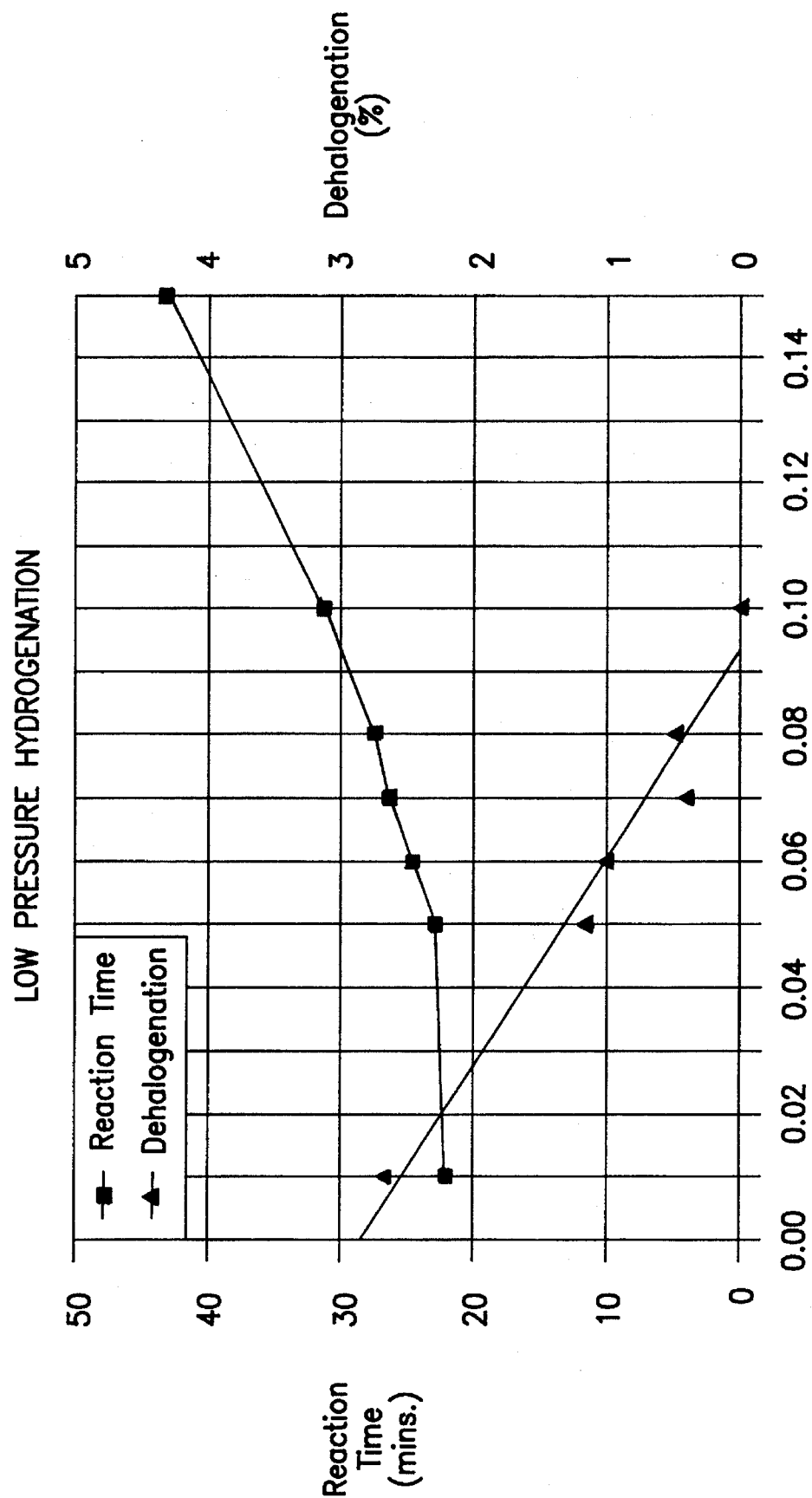

The catalyst according to the invention has better hydrogenation activity than known catalysts for a low noble metal demand of only 0.1 to 5.0% by weight and preferably 0.5 to 3.5% by weight. The selectivity of the catalyst is improved over the prior art by addition of a small quantity of copper. The ratio by weight of platinum to copper may be between 5:1 and 20:1 and is preferably 10:1. Where the support is charged with 1% by weight platinum, this corresponds to 0.1% by weight copper.

The excellent properties of the catalyst according to the invention are based on the combination of active carbon support with a suitable charge of platinum and copper. A suitable active carbon support is described in DE-PS 38 23 301. It has a BET surface of >500 $m^2/g$, a total pore volume of >0.5 ml/g and an ash content of <5% by weight. Its mean particle size is 15 to 30 µm. A particularly useful active carbon support has a BET surface area of 1000 $m^2/g$, and a total pore volume of 1.01 ml/g. The upper limit of surface area and pore volume is not narrowly critical and can vary widely as will be apparent to those skilled in the art after studying this invention. One suitable range is from >500 $m^2/g$ to about 1000 $m^2/g$ surface area, and a pore volume from >0.5 ml/g to about 1.01 ml/g.

The production process according to the invention uses known water-soluble platinum compounds, preferably hexachloroplatinic acid, and known copper salts, such as copper acetate, copper chloride, copper nitrate and copper sulfate. The use of copper acetate is particularly favorable. Platinum and copper are precipitated from the solution as hydroxide compounds by addition of a base and are deposited on the support. To achieve optimal dispersion of the metal over the particles of active carbon, it is important that precipitation and subsequent reduction of the hydroxide compounds are carried out at temperatures in the range from 70° to 100° C. A catalyst in which platinum and copper are present in fine-particle, reduced form on active carbon is formed in this elevated temperature range.

Impregnation of the active carbon with the metal compounds may be carried out by precipitation of the two metal components from the solution either simultaneously, as described above, or successively. In the case of separate precipitation, the active carbon is impregnated first with platinum and then in a second step with copper.

The invention is illustrated by the following Examples. Example 1 describes the production of catalysts according to the invention and comparison catalysts from the prior art. In Examples 2 to 4, the catalysts were tested and compared with one another for activity and selectivity in an adiabatic high-pressure test, an isothermal high-pressure test and in a low-pressure test. In Example 5, multicycle hydrogenations were carried out with a sulfur-modified standard and with a catalyst according to the invention to compare their long-term stability. The results of the Examples are set out in Tables 1 to 5 and illustrated in the sole FIGURE.

EXAMPLE 1

Catalyst Production

Active carbon having the following material data was used as the support for all the catalysts:

| Material active carbon | |
|---|---|
| Specific BET surface | 1,000 m²/g (ASTM-D-3663) |
| Total pore volume | 1.01 ml/g (ASTM-D-4284) |
| Apparent density | 210 g/l |
| Mean particle size | 24.0 μm (ASTM-D-4464) |

A) Production of the catalysts according to the invention

To produce a catalyst according to the invention charged with 1% platinum and 0.1% by weight copper, 100 g active carbon were stirred into distilled water at a speed of 300 r.p.m. Aqueous solutions of 2.5 g hexachloroplatinic acid hexahydrate (corresponds to 1 g Pt) and 0.316 g copper acetate monohydrate (corresponds to 0.1 Cu) were introduced into the resulting suspension and the suspension was then heated to 80° C. Sodium hydroxide was then added with continuously stirring to precipitate the hydroxides. Finally, 0.3 ml 37% formaldehyde solution was added to reduce the metal compounds. The temperature of the suspension was also kept constant at 80° C. during the reduction step. After the reduction step, the catalyst was filtered off through a nutsche and washed with distilled water. The catalyst was used for the hydrogenation in the wet state. Catalysts according to the invention differing in their platinum and copper contents were produced by correspondingly increasing the quantities of hexachloroplatinic acid, copper acetate and sodium hydroxide.

B) Production of comparison catalysts

Pure platinum/active carbon catalysts and sulfur-modified platinum/active carbon catalysts were produced for comparison with the catalysts according to the invention. Production was carried out in the same way as described in A) except that no copper acetate was added. The modification with sulfur was carried out by the process described in DE-PS 21 50 220.

Table 1 lists all the catalysts produced for the comparison tests of Examples 2 to 5. The catalysts according to the invention are identified by the letters C and consecutive numbering. Catalysts C 1 to C 4 differ from one another in the charging of the catalyst support with platinum. The ratio by weight between platinum and copper is 10:1. Comparison catalysts CC 1.1, CC 3.1, CC 4.1 from the prior art correspond to catalysts C 1, C 3 and C 4, but are not modified with copper. By contrast, comparison catalysts CC 1.2, CC 3.2 and CC 4.2 are modified with sulfur (sulfidized) in accordance with the prior art.

In order to test the influence of the ratio by weight of platinum to copper, catalysts C 5 to C 11 were produced with different copper charges of 0.01% to 0.15% for the same platinum charge of 1%.

TABLE 1

Comparison of Catalysts

| | | Content | | |
|---|---|---|---|---|
| | | Pt | Cu | S |
| Catalyst | C 1 | 1% | 0.1% | — |
| Catalyst | C 2 | 2% | 0.2% | — |
| Catalyst | C 3 | 3% | 0.3% | — |
| Catalyst | C 4 | 5% | 0.5% | — |
| Comparison catalyst | CC 1.1 | 1% | — | — |
| Comparison catalyst | CC 3.1 | 3% | — | — |
| Comparison catalyst | CC 4.1 | 5% | — | — |
| Comparison catalyst | CC 1.2 | 1% | — | Sulfidized |
| Comparison catalyst | CC 3.2 | 3% | — | Sulfidized |
| Comparison catalyst | CC 4.2 | 5% | — | Sulfidized |
| Catalyst | C 5 | 1% | 0.01% | — |
| Catalyst | C 6 | 1% | 0.05% | — |
| Catalyst | C 7 | 1% | 0.06% | — |
| Catalyst | C 8 | 1% | 0.07% | — |
| Catalyst | C 9 | 1% | 0.08% | — |
| Catalyst | C 10 | 1% | 0.10% | — |
| Catalyst | C 11 | 1% | 0.15% | — |

EXAMPLE 2

Adiabatic High-Pressure Hydrogenations of 3,4-dichloronitrobenzene With Various Catalysts The hydrogenations were carried out in a 500 ml Hastelloy autoclave. 75 g 3,4-dichloronitrobenzene dissolved in 125 ml toluene and 0.375 g catalyst (dry matter), corresponding to 0.5% by weight catalyst based on dichloronitrobenzene, were used. The catalyst quantity of 0.375 g dry matter was used in the case of the catalysts charged with 1% platinum. In the case of the catalysts charged with 3% and 5% platinum, only ⅓ rd and ⅕ th of the above quantity was used.

TABLE 2

Adiabatic high-Pressure hydrogenation of 3,4-dichloro-nitrobenzene

| | Charge | | | | Gas chromatography | | |
|---|---|---|---|---|---|---|---|
| Catalyst | Pt [% by weight] | Cu [% by weight] | t [mins.] | Tmax [°C.] | DCA | DCNB | Dehalo |
| C 1 | 1 | 0.1 | 6.0 | 106.0 | 100 | 0 | 0 |
| C 3 | 3 | 0.3 | 14.5 | 78.0 | 100 | 0 | 0 |
| C 4 | 5 | 0.5 | 30.0 | 62.0 | 100 | 0 | 0 |
| CC 1.1 | 1 | — | 4.0 | 127.0 | 99.1 | 0 | 0.9 |
| CC 3.1 | 3 | — | 7.0 | 89.0 | 99.4 | 0 | 0.6 |
| CC 4.1 | 5 | — | 13.0 | 78.5 | 99.5 | 0 | 0.5 |
| CC 1.2 | 1 | Sulfidized | 6.0 | 100.0 | 100 | 0 | 0 |
| CC 3.2 | 3 | Sulfidized | 20.5 | 71.0 | 100 | 0 | 0 |
| CC 4.2 | 5 | Sulfidized | 34.5 | 60.5 | 100 | 0 | 0 |

DCNB = 3,4-Dichloronitrobenzene (educt)
DCA = 3,4-Dichloroaniline (product)
Dehalo = Dehalogenation products
t = Reaction time to Tmax
Tmax = Maximum temperature The hydrogenation pressure in the hydrogenation tests was 60 bar and the starting temperature was 40° C. The reaction mixture was continuously stirred during the hydrogenation and both the temperature and the hydrogen consumption were measured.

The hydrogenation of dichloronitrobenzene is exothermic. Accordingly, the temperature of the reaction mixture rose to a maximum value in a few minutes under the effect of the heat generated and then fell slowly.

The time taken to reach the maximum temperature is shown in Table 2 as the "reaction time t" together with the maximum temperature Tmax. The reaction mixtures were analyzed by gas chromatography after 1 hour.

Table 2 shows that, in all the tests, none of the 3,4-dichloronitrobenzene (DCNB) used as educt could be detected in the reaction mixture after a reaction time of 1 hour. In the case of the copper-modified catalysts C 1, C 3 and C 4 according to the invention, no dehalogenation products (dehalo) could be detected whereas the unmodified comparison catalysts CC 1.1, CC 3.1 and CC 4.1—although showing higher activity—produce dehalogenation products and hence show poorer selectivity than the catalysts according to the invention.

The sulfur-modified comparison catalysts are similar in their activity to the catalysts according to the invention under the described test conditions and also produce no dehalogenation products. However, as Example 5 will show, their long-term stability is considerably poorer than that of the catalysts according to the invention.

EXAMPLE 3

Isothermal High-Pressure Hydrogenation of 3,4-dichloronitrobenzene

The isothermal high-pressure hydrogenations were carried out in a 1 liter autoclave of V4A steel. Catalysts C 1, C 2 and C 3 according to the invention and comparison catalyst CC 1.2, a sulfur-modified standard catalyst, were used.

The isothermal hydrogenations were carried out under the following test conditions:

| Quantities weighed in | 100 g 3,4-DCNB (3,4-dichloronitrobenzene) |
| --- | --- |
| | 520 g toluene |
| | 0.2% catalyst dry matter, based on DCNB |
| Temperature | T = 100° C. |
| H₂ pressure | p = 60 bar |
| Stirrer speed | n = 1,150 r.p.m. |

The content of the desired product, 3,4-dichloroaniline (3,4-DCA), in the reaction mixtures was tested at regular intervals. The results are set out in Table 3. All the catalysts showed 100 selectivity, i.e. no dehalogenation products could be detected after complete hydrogenation. However, the copper-modified platinum catalysts according to the invention showed higher activity than the sulfur-modified standard catalyst CC 1.2.

TABLE 3

Isothermal high-pressure hydrogenation of 3,4-dichloronitrobenzene

| | Charge | | | | | | | |
| --- | --- | --- | --- | --- | --- | --- | --- | --- |
| | Pt [% by | Cu [% by | Hydrogenation time [mins.] | | | | | |
| Catalyst | weight] | weight] | 20 | 40 | 60 | 90 | 120 | 140 |
| CC 1.2 | 1 | Sulfidized | 34.2 | 52.0 | 61.1 | 77.7 | 91.4 | 96.9 |
| C 1 | 1 | 0.1 | 45.2 | 62.5 | 81.2 | 97.8 | 100 | — |
| C 2 | 2 | 0.2 | 56.0 | 86.6 | 99.3 | 100 | — | — |
| C 3 | 3 | 0.3 | 88.1 | 99.1 | 99.3 | — | — | — |

(figures in % 3,4-DCA)

EXAMPLE 4

Low-pressure Hydrogenation of 3,4-dichloronitrobenzene

The low-pressure hydrogenations were carried out in a glass reactor into which the reaction mixture was introduced at atmospheric pressure and then placed under a slight partial pressure of hydrogen gas. The test conditions were as follows:

| Quantities weighed in | 10 g 3,4-dichloronitrobenzene (3,4-DCNB) |
| --- | --- |
| | 110 ml ethanol |
| | 500 mg catalyst dry matter |
| Temperature | T = 40° C. |
| H₂ partial pressure | p = 10 mbar |
| Stirrer speed | n = 2,000 r.p.m. |

Catalysts C 5 to C 11 according to the invention with different platinum-to-copper ratios were used for the low-pressure hydrogenations. The results are set out in Table 4. In addition to the reaction time RT, Table 4 shows the hydrogen consumption in that time and the gas chromatographic analyses of the product mixture. In this case, the reaction time RT is the time which the hydrogen consumption takes to fall to 10 ml/min.

Table 4 shows that the reaction time increases with increasing copper content, i.e. the activity of the catalyst is reduced. At the same time, however, the percentage content of dehalogenation products decreases and disappears completely at a platinum-to-copper ratio of 10:1.

This situation is graphically illustrated in FIG. 1 which shows the singularity of the catalyst composition according to the invention.

TABLE 4

Low-pressure hydrogenation of 3,4-dichloronitrobenzene

| | Charge | | | | Gas chromatography [%] | |
| --- | --- | --- | --- | --- | --- | --- |
| | Pt | Cu | RT | H₂ consumption | | |
| Catalyst | [%] | [%] | [mins.] | [ml] | DCA | Dehalo |
| C 5 | 1 | 0.01 | 22.2 | 2750 | 97.3 | 2.7 |
| C 6 | 1 | 0.05 | 22.9 | 2760 | 98.8 | 1.2 |
| C 7 | 1 | 0.06 | 24.5 | 2680 | 99.0 | 1.0 |
| C 8 | 1 | 0.07 | 26.4 | 2670 | 99.6 | 0.4 |
| C 9 | 1 | 0.08 | 27.2 | 2650 | 99.5 | 0.5 |
| C 10 | 1 | 0.10 | 31.0 | 2590 | 100.0 | 0.0 |

TABLE 4-continued

Low-pressure hydrogenation of 3,4-dichloronitrobenzene

| | Charge | | | | Gas chromatography [%] | |
|---|---|---|---|---|---|---|
| Catalyst | Pt [%] | Cu [%] | RT [mins.] | $H_2$ consumption [ml] | DCA | Dehalo |
| C 11 | 1 | 0.15 | 42.8 | 2350 | 100.0 | 0.0 |

DCA: 3,4-dichloroaniline
Dehalo: Dehalogenation products
RT: Reaction time for the hydrogen consumption to fall to 10 ml/min.

EXAMPLE 5

Adiabatic Multicycle Hydrogenation of 3,4-dichloronitrobenzene

The hydrogenations were carried out in a 500 ml Hastelloy autoclave. The autoclave used in Example 5 differed from the autoclave in Example 2 in its stirrer characteristic and heat dissipation properties. Catalyst C 1 according to the invention and the sulfur-modified comparison catalyst CC 1.2 were used. The test conditions and quantities used were the same as in Example 2. To test long-term stability, several batches of 3,4-dichloronitrobenzene were hydrogenated with each catalyst sample. To this end, the catalyst was filtered off from the product after each hydrogenation and reused for the next hydrogenation.

The results of Table 5 show that the catalyst according to the invention has better activity (shorter hydrogenation times) than the standard catalyst coupled with a uniformly high selectivity. The differences between the two catalysts in regard to yield are particularly dramatic. Whereas the catalyst according to the invention still gives a yield of 91.4% in the third hydrogenation cycle, the yield has fallen to 54.4% in the third hydrogenation cycle where the standard catalyst is used.

Further variations and modifications of the present invention will be apparent to those skilled in the art from the foregoing and are intended to be encompassed by the claims appended hereto.

German priority application P 42 18 866.0 is relied on and incorporated herein by reference.

TABLE 5

Multicycle hydrogenation of 3,4-dichloronitrobenzene

| Catalyst | Cycle | t [mins.] | Tmax [ml] | Yield [%] | Selectivity [%] |
|---|---|---|---|---|---|
| C 1 | 1 | 14 | 96 | 100.0 | 99.6 |
| | 2 | 22 | 87 | 98.2 | 99.4 |
| | 3 | 26 | 86 | 91.4 | 99.3 |
| CC 1.2 | 1 | 28 | 86 | 97.6 | 96.8 |
| | 2 | 29 | 80 | 65.4 | 100.0 |
| | 3 | 33 | 80 | 54.4 | 95.0 | t: Reaction time to Tmax
Tmax: Maximum reaction temperature

We claim:

1. A modified noble metal supported catalyst for the selective hydrogenation of aromatic halonitro compounds and to form aromatic haloamines comprising an active carbon support having specific surface area of greater than 500 $m^2/g$, platinum as the catalytically active component and copper as modifier, wherein platinum is present in a quantity of 0.1 to 5.0% by weight based on said active carbon support, and the ratio by weight between said platinum and said copper simultaneously present is 5:1 to 20:1, and said platinum and copper are present in fine distribution on said active carbon support.

2. The catalyst as claimed in claim 1, wherein the mean particle diameter of the active carbon is 15 to 30 μm, its specific surface area is greater than 500 $m^2/g$ and its total pore volume is greater than 0.5 ml/g.

3. The catalyst as claimed in claim 1 wherein the platinum is present in a quantity of 0.5 to 3.5% by weight.

4. The catalyst as claimed in claim 1 wherein said ratio is 10:1.

5. The catalyst as claimed in claim 2 wherein the surface area range from greater than 500 $m^2/g$ to about 1000 $m^2/g$.

6. The catalyst as claimed in claim 2 wherein the total pore volume ranges from greater than 0.5 ml/g to about 1.01 ml/g.

7. The catalyst as claimed in claim 2 wherein the platinum and copper are present in fine particle, reduced form on active carbon.

8. A process for the production of a supported noble metal catalyst comprising impregnating an active carbon support having a specific surface area of greater than 500 $m^2/g$ suspended in water with a water soluble compound of platinum and a water soluble compound of copper, precipitating said compounds from aqueous solutions of readily soluble compounds thereof, and reducing the catalyst; wherein said precipitating and reducing are at a temperature of from 70° to 100° C.

9. The process as claimed in claim 8 wherein hexachloroplatinic acid is the water soluble platinum compound.

10. The process as defined in claim 8 wherein copper acetate is the water soluble copper compound.

11. The process as defined in claim 8 wherein the content of platinum metal and copper metal in the solution are gauged to correspond to the desired charge of the quantity of active carbon used.

12. The process as defined in claim 8 wherein the suspension is heated with stirring to 70° to 100° C. together with the solution of the water-soluble platinum and copper compounds before platinum and copper are simultaneously deposited on the active carbon by addition of a base.

13. The process as defined in claim 12 wherein the base is sodium carbonate or sodium hydroxide in the form of their sparingly soluble compounds.

14. The process as defined in claim 12 wherein the platinum and copper are subsequently reduced at the same temperature by addition of a reducing agent.

15. The process as defined in claim 14 wherein the reducing agent is hydrazine, sodium formate, sodium boranate or formaldehyde.

16. The process as defined in claim 8 wherein an aqueous suspension is formed containing 5 to 30% by weight active carbon as the catalyst support.

17. A modified noble metal catalyst made by a process consisting essentially of impregnating an active carbon support suspended in water with a water soluble compound of platinum and a water soluble compound of copper, precipitating said compounds from aqueous solutions of readily soluble compounds thereof, reducing the catalyst, and optionally filtering and washing the catalyst; wherein said precipitating and reducing are at a temperature of from 70° to 100° C.

18. The catalyst according to claim 1, consisting essentially of an active carbon support having a specific surface area of greater than 500 m²/g, platinum as the catalytically active component and copper as modifier, wherein platinum is present in a quantity of 0.1 to 5.0% by weight based on said active carbon support, and the ratio by weight between said platinum and said copper simultaneously present is 5:1 to 20:1, and said platinum and copper are present in fine distribution on said active carbon support.

19. The process according to claim 8, consisting essentially of impregnating an active carbon support having a specific surface area of greater than 500 m²/g suspended in water with a water soluble compound of platinum and a water soluble compound of copper, precipitating said compounds from aqueous solutions of readily soluble compounds thereof, reducing the catalyst, and optionally filtering and washing the catalyst; wherein said precipitating and reducing are at a temperature of from 70° to 100° C.

20. The process according to claim 8, further comprising filtering and washing the catalyst.

\* \* \* \* \*